United States Patent [19]
Irie et al.

[11] Patent Number: 5,574,121
[45] Date of Patent: Nov. 12, 1996

[54] PROCESS FOR PREPARING AN ABSORBENT RESIN CROSSLINKED WITH A MIXTURE OF TRIMETHYLOLPROPANE DIACRYLATE AND TRIACRYLATE

[75] Inventors: Yoshio Irie, Himeji; Nobuyuki Harada, Suita; Kinya Nagasuna, Himeji; Kohichi Hirota, Kobe; Yoshihiko Masuda, Takarazuka; Hideaki Nagano; Hideyuki Kubo, both of Himeji, all of Japan

[73] Assignee: Nippon Shokubai Co., Ltd., Osaka, Japan

[21] Appl. No.: 262,065

[22] Filed: Jun. 17, 1994

[30] Foreign Application Priority Data

Jun. 18, 1993 [JP] Japan ................................. 5-147533
Dec. 28, 1993 [JP] Japan ................................. 5-335810

[51] Int. Cl.$^6$ ................................................. C08F 236/22
[52] U.S. Cl. ........................ 526/318.44; 525/330.2; 526/318.4; 526/318.43; 526/320; 526/321; 526/323.1; 526/323.2; 526/930
[58] Field of Search ...................... 525/330.2; 526/318.4, 526/323.2, 930, 318.43, 318.44

[56] References Cited

U.S. PATENT DOCUMENTS

| | | | |
|---|---|---|---|
| 4,076,663 | 2/1978 | Masuda | 525/54.31 |
| 4,286,082 | 8/1981 | Tsubakimoto et al. | 526/240 |
| 4,377,661 | 3/1983 | Wright | 524/522 |
| 4,654,039 | 3/1987 | Brandt | 604/368 |
| 4,833,222 | 5/1989 | Sidall et al. | 526/200 |
| 4,920,187 | 4/1990 | Kashihara | 526/193 |

FOREIGN PATENT DOCUMENTS

| | | |
|---|---|---|
| 0031628A2 | 7/1981 | European Pat. Off. |
| WO90/15830 | 12/1990 | WIPO . |
| WO9051830 | 12/1990 | WIPO . |

*Primary Examiner*—Fred Zitomer
*Attorney, Agent, or Firm*—Ronald J. Kubovcik

[57] ABSTRACT

A process for preparing an absorbent resin includes the steps of: preparing a first crosslinking agent (A) including at least two polymerizable unsaturated bonds; preparing a second crosslinking agent (B) including at least two polymerizable unsaturated bonds and hydroxyl groups; preparing a crosslinking agent including (A) and (B) with a ratio of (A) to (B) ranging from 95/5 to 50/50; and polymerizing a hydrophilic unsaturated monomer having at least one carboxyl group using the crosslinking agent. The crosslinking agent includes a crosslinking agent which includes a main component at least 90 percent by weight, the main component being an ester having at least two polymerizable unsaturated bonds, wherein the ester is composed of a polyhydroxy alcohol (C) having not more than six carbon atoms and at least three hydroxy groups, and an unsaturated carboxylic acid (D); and a molecular weight ratio of the main component to a standard compound (E) is in the range of from 0.7/1 to less than 1.3/1, (E) being an ester composed of (C) that composes the main component, and (D) that composes the main component, in which all the hydroxy groups in (C) are ester-linked with (D).

29 Claims, No Drawings

PROCESS FOR PREPARING AN ABSORBENT RESIN CROSSLINKED WITH A MIXTURE OF TRIMETHYLOLPROPANE DIACRYLATE AND TRIACRYLATE

FIELD OF THE INVENTION

The present invention relates to a process for preparing an absorbent resin, more specifically relates to a process for preparing an absorbent resin which exhibits excellent properties including its gel stability, diffusivity of aqueous liquid and permeability to aqueous liquid, suitable for use in sanitary goods.

BACKGROUND OF THE INVENTION

Recently, an absorbent resin is widely used in sanitary goods such as paper diaper's, sanitary napkins, etc., for the purpose of absorbing liquid.

Examples of the conventionally known absorbent resins includes: a partially neutralized crosslinked polymer of polyacrylic acid (Japanese Unexamined Patent Publication No. 84304/1980 (Tokukaisho 55-84304), Japanese Unexamined Patent Publication No. 108407/1980 (Tokukaisho 55-108407) and Japanese Unexamined Patent Publication No. 133413/1980 (Tokukaisho 55-133413)); a hydrolyzed polymer of starch-acrylonitrile (Japanese Unexamined Patent Publication No. 43995/1971 (Tokukaisho 46-43995)); a neutralized graft polymer of starch-acrylic acid (Japanese Unexamined Patent Publication No. 125468/1976 (Tokukaisho 51-125468)); a saponified copolymer of vinyl acetate-acrylic ester (Japanese Unexamined Patent Publication No. 14689/1977 (Tokukaisho 52-14689)); a hydrolyzed copolymer of acrylonitrile or of acrylamide (Japanese Unexamined Patent Publication No. 15959/1978 (Tokukaisho 53-15959)); a crosslinked polymer of cationic monomer (Japanese Unexamined Patent Publication No. 154709/1983 (Tokukaisho 53-154709) and Japanese Unexamined Patent Publication No. 154710/1983 (Tokukaisho 58-154710)).

Among the above-listed crosslinked polymers, a crosslinked polymer obtained by polymerizing a hydrophilic unsaturated monomer having at least one carboxyl group such as acrylic acid in the presence of a crosslinking agent is the most common material for the absorbent resin, because a raw material for the above polymer is available at low price, while exhibiting excellent absorbent properties without the problem of putrefaction.

The absorbent resin desirably exhibits the following properties when it is in contact with an aqueous liquid: high magnifier and rate of absorbency; an excellent stability of its swollen gel; high diffusivity of and permeability to aqueous liquid, a strong suction power for sucking the aqueous liquid from the material containing aqueous liquid, etc.

Recently, still thinner sanitary goods of higher quality have been demanded, and an amount of use of the absorbent resin has been increasing. Thus, an absorbent resin which exhibits improved gel stability, diffusivity of and permeability to aqueous liquid is strongly demanded. As well known, these properties of the absorbent resin are greatly affected by a crosslinking agent used in the preparation process of the absorbent resin.

The crosslinking agent used in the preparation of the absorbent resin must be commercially available and safe, and it is also required to exhibit excellent affinity and polymerizability with a hydrophilic unsaturated monomer. For the above mentioned absorbent resin, unsaturated carboxylates of polyhydroxy alcohol, which have a plurality of polymerizable unsaturated groups and are polymerizable with a hydrophilic unsaturated monomer having at least one carboxyl group may be used. Examples of the above unsaturated carboxylates include: di(meth) acrylate of polyoxyalkylene glycol, (poly)propylene glycol di(meth)acrylate, trimethylolpropane tri(meth)acrylate, pentaerythritol tetra(meth)acrylate, dipentaerythritol hexamethacrylate, and the like.

In order to prepare the absorbent resin which exhibits an excellent gel stability and diffusivity of aqueous liquid using one of the above-listed unsaturated carboxylates as a crosslinking agent, the crosslinking agent must be used in a large amount. Here, the amount of use of the crosslinking agent and the gel stability have a virtually positive relationship. However, because of other factors, such as copolymerizability, affinity and solubility of the crosslinking agent and the hydrophilic unsaturated monomer having at least one carboxyl group, etc., the reactivity of the crosslinking agent is lowered when it is used in an excess amount of a predetermined range. Namely, the excessive amount of the crosslinking agent would not give an improvement in the above properties of the absorbent resin as much as expected for the amount of use of the crosslinking agent. Moreover, the effect of reducing the water soluble polymer content, which affects the diffusivity of and permeability to aqueous liquid of the absorbent resin, is reduced. Thus, in order to obtain absorbent resin which exhibits an excellent gel stability, a large amount of the crosslinking agent is required.

In order to improve the copolymerizability, affinity and solubility of the crosslinking agent and the hydrophilic unsaturated monomer, for example, a method for polymerizing in the presence of a surface active agent (Japanese Examined Patent Publication No. 36763/1986 (Tokukosho 61-36763)) and a method for polymerizing in the presence of a dispersant (Japanese Unexamined Patent Publication No. 146902/1989 (Tokukohei 1-146902) are disclosed. However, since all of the above methods present the problem that the surface active agent or the dispersant remains in the resulting absorbent resin, which lowers the absorbent properties of the resulting absorbent resin, they are not desirable.

SUMMARY OF THE INVENTION

An object of the present invention is to provide a process for preparing an absorbent resin which exhibits excellent properties including its gel stability, diffusivity of aqueous liquid and permeability to aqueous liquid with low water soluble polymer content, which are suitable for use in sanitary goods, without having therein by-products such as a surface active agent or dispersant remaining as residues nor requiring a large amount of crosslinking agents.

In order to achieve the above object, the inventors of the present invention examined a process for preparing the absorbent resin with respect to polymerizing a hydrophilic unsaturated monomer having at least one carboxyl group in the presence of a crosslinking agent having at least two polymerizable unsaturated bonds, and discovered that by mixing or combining the crosslinking agent having at least two polymerizable unsaturated bonds at a predetermined ratio with another crosslinking agent having at least two polymerizable unsaturated bonds and hydroxy groups, the above-mentioned problems would be solved. The inventors of the present invention also discovered that in the case of using an ester of the polyhydroxy alcohol having at least three hydroxy groups and the unsaturated carboxyl acid as the crosslinking agent, if more than a predetermined amount of a high boiling-point compound having at least two polyhydroxy alcohol structures in a molecule is included, it would be difficult to achieve the improved absorbent properties of the absorbent resin. This means that the above problem can be prevented also by adjusting the content of the high boiling-point compound present in the crosslinking agent.

In order to achieve the above object, the first process for preparing the absorbent resin in accordance with the present invention is characterized by comprising the steps of:

preparing the first crosslinking agent including at least two polymerizable unsaturated bonds;

preparing the second crosslinking agent including at least two polymerizable unsaturated bonds and hydroxy groups;

preparing a crosslinking agent including the first crosslinking agent and the second crosslinking agent with a ratio of the weight of the first crosslinking agent to the weight of the second crosslinking ranging from 95/5 to 50/50; and polymerizing a hydrophilic unsaturated monomer having at least one carboxyl group using the crosslinking agent.

The second process for preparing an absorbent resin is characterized by including the step of:

polymerizing a hydrophilic unsaturated monomer having at least one carboxyl group using a crosslinking agent which includes a main component at least 90 percent by weight, the main component being an ester having at least two polymerizable unsaturated bonds, wherein the ester is composed of: a polyhydroxy alcohol having not more than six carbon atoms and at least three hydroxy groups; and an unsaturated carboxylic acid; and a molecular weight ratio of the main component to a standard compound is in the range of from 0.7/1 to less than 1.3/1, the standard compound being an ester composed of: the polyhydroxy alcohol that composes the main component, and the unsaturated carboxylic acid that composes the main component, in which all the hydroxy groups in the polyhydroxy alcohol are ester-linked with the unsaturated carboxylic acid.

The above processes give improved copolymerizability, affinity and solubility, etc., between the crosslinking agent and the hydrophilic unsaturated monomer and gives a simple process for preparing the absorbent resin which exhibits improved properties including stability and strength of the gel, and the diffusivity of and permeability to aqueous liquid with low water soluble polymer content, suitable for use in sanitary goods without having therein by-products such as a surface active agent or dispersant therein as residues nor requiring a large amount of the crosslinking agent.

The following descriptions will describe the present invention in detail.

Examples of hydrophilic unsaturated monomer having at least one carboxyl group used as a raw material for the absorbent resin of the present invention include: acrylic acid, methacrylic acid, maleic acid, maleic anhydride, β-acryloxypropionic acid, fumaric acid, crotonic acid, itaconic acid, sorbic acid, cinnamic acid or the above acids in a neutralized form. The hydrophilic unsaturated monomer may be one of the above listed acids or a combination or mixture thereof. Among the above-listed acids, the acrylic acid, methacrylic acid and these acids in a neutralized form are particularly preferable.

Generally, the affinity and solubility between the hydrophilic unsaturated monomer and the crosslinking agent is lowered when the carboxyl groups in the monomer are neutralized. On the contrary, the advantages of the process according to the present invention become particularly clear when the carboxyl groups in the monomer are neutralized. Therefore, it is particularly preferable that the acrylic acid and the methacrylic acid present in the partially neutralized form in the range from 30 mole percent to 90 mole percent of all carboxyl groups, with a more preferred range being from 50 mole percent to 80 mole percent and the most preferred range being from 60 mole percent to 75 mole percent.

The above hydrophilic unsaturated monomer used as a raw material for the absorbent resin may be combined or mixed with another unsaturated monomer if necessary. Although the material for this additionally used monomer is not specified in the present invention, for example, the following materials may be used: an anionic unsaturated monomer such as vinylsulfonic acid, styrenesulfonic acid, 2-(meth)acrylamide-2-metylpropanesulfonic acid, 2-(meth)acryloylethanesulfonic acid, 2-(meth)acryloylpropanesulfonic acid, etc., and salts thereof; a nonionic unsaturated monomer including hydrophilic groups such as acrylamide, methacrylamide, N-ethyl(meth)acrylamide, N-n-propyl-(meth)acrylamide, N-isopropyl(meth)acrylamide, N,N-dimethyl(meth)acrylamide, 2-hidroxylethyl(meth)acrylate, 2-hydroxylpropyl(meth)acrylate, methoxypolyethylene glycol (meth)acrylate, polyethylene glycol mono(meth)acrylate, vinylpyridine, N-vinylpyrrolidone, N-acryloylpiperidine, N-acryloylpyrrolidine and the like; a cationic unsaturated monomer such as N,N-dimethylaminoethyl(meth)acrylate, N,N-diethylaminoethyl(meth)acrylate, N,N-dimethylaminopropyl(meth)acrylate, N,N-diethylaminopropyl(meth)acrylate and quaternary salts thereof and the like. The above additional hydrophilic unsaturated monomer is preferably is used in an amount not more than 50 percent by weight to the total weight of the hydrophilic unsaturated monomers including the original hydrophilic unsaturated monomer having at least one carboxyl group.

As described, the crosslinking agent used in the polymerization in the first process for preparing the absorbent resin of the present invention includes the first crosslinking agent having at least two polymerizable unsaturated bonds and the second crosslinking agent having at least two polymerizable unsaturated bonds and at least one hydroxy group at a ratio of the weight of the first crosslinking agent to the weight of the second crosslinking agent ranging from 95/5 to 50/50.

The first crosslinking agent may be at least one material selected from the group consisting of N,N'-methylenebis(meth)acrylamide, (poly)ethylene glycol di(meth)acrylate, (poly)propylene glycol di(meth)acrylate, 1,4-butanediol di(meth)acrylate, 1,5-pentanediol (meth)acrylate, 1,6-hexanediol di(meth)acrylate, neopentyl glycol diacrylate, trimethylolpropane tri(meth)acrylate, ethylene oxide denatured trimethylolpropane tri(meth)acrylate, glycerin tri(meth)acrylate, pentaerythritol tetra(meth)acrylate, ditrimethylolpropane tetra(meth)acrylate, dipentaerythritol hexa(meth)acrylate, tetramethylolmethane tetraacrylate, triallyl cyanurate, triallyl isocyanurate, triallylamine and tetraallyloxyethane. For the first crosslinking agent, those exhibiting low affinity and solubility with the hydrophilic unsaturated monomer having at least one carboxyl group (especially in a neutralized form) is preferable because the advantages of the process according to the present invention become clear.

The first crosslinking agent preferably includes at least three polymerizable unsaturated bonds in consideration of the gel strength, water soluble polymer content, etc., of the resulting absorbent resin. The first crosslinking agent may be at least one material selected from the group consisting of trimethylolpropane tri(meth)acrylate, ethylene oxide denatured trimethylolpropane tri(meth)acrylate, pentaerythritol tetra(meth)acrylate, triallylamine and tetraallyloxyethane.

The second crosslinking agent may be at least one material selected from the group consisting of trimethylolpropane di(meth)acrylate, ethylene oxide denatured trimethylolpropane di(meth)acrylate, glycerin acrylate methacrylate, glycerin di(meth)acrylate, pentaerythritol tri(meth)acrylate, dipentaerythritol penta(meth)acrylate, tetramethylolmethane triacrylate, reaction product of polyhydroxy epoxy compound and (meth)acrylic acid and the like.

The second crosslinking agent preferably has a structure similar to the first crosslinking agent and exhibits excellent affinity with the first crosslinking agent because improved affinity and the solubility of the first crosslinking agent with the hydrophilic unsaturated monomer having at least one carboxyl group (especially in a neutralized form) can be achieved.

The second crosslinking agent in accordance with the present invention is preferably at least one material selected from the group consisting of trimethylolpropane di(meth)acrylate, ethylene oxide denatured trimethylolpropane di(meth)acrylate and pentaerythritol tri(meth)acrylate.

As a typical example of the first crosslinking agent and the second crosslinking agent, an ester of polyhydroxy alcohol having at least three hydroxy groups and an unsaturated carboxylic acid may be raised. Here, if the first crosslinking agent and the second crosslinking agent have the same polyhydroxy alcohol structure, it would not be necessary to prepare the two crosslinking agents separately. As long as the ratio of the compound of the first crosslinking agent to the compound of the second crosslinking agent falls within a predetermined range of the present invention by adjusting the conditions for the esterification process, a compound resulting from a sole esterification may be used directly as the crosslinking agent in the first process for preparing the absorbent resin of the present invention.

In the esterification process, a high boiling-point compound having at least two polyhydroxy alcohol structures in a molecule may be generated as a by-product. However, as long as the ratio of the first crosslinking agent to the second crosslinking agent in the total crosslinking agent falls within the predetermined range, the high boiling-point compound may be included in a range of from above 0 percent by weight to less than 30 percent by weight with a more preferred range being from 10 percent by weight to 20 percent by weight.

In the first process for preparing an absorbent resin of the present invention, the ratio of the first crosslinking agent to the second crosslinking agent is set in a range of from 95/5 to 50/50. When the second crosslinking agent is used in a reduced amount of the above mentioned range, the desirable affinity and solubility between the first crosslinking agent in the relatively large amount and the monomer are difficult to be achieved. Moreover, improvements in the other properties of the absorbent resin such as the gel strength, the water soluble polymer content are also difficult to be achieved. On the other hand, when the second crosslinking agent is used in an excess amount of the above mentioned range, the properties of the first crosslinking agent used in a relatively small amount are hardly shown, and the gel strength may be lowered or the physical properties of the absorbent resin such as the magnifier of the absorbency may not be controlled. Therefore, the ratio of the first crosslinking agent to the second crosslinking agent is preferably set in a range of from 90/10 to 60/40. Additionally, it is preferable that the total amount of the crosslinking agent is set in a range of from about 0.05 mole percent to 1 mole percent with respect to the hydrophilic unsaturated monomer having at least one carboxyl group.

The second process for preparing an absorbent resin of the present invention is characterized in that a hydrophilic unsaturated monomer having at least one carboxyl group is polymerized using a crosslinking agent which includes a main component at least 90 percent by weight. The main component of the crosslinking agent is an ester having at least two polymerizable unsaturated bonds, which is composed of a polyhydroxy alcohol having not more than six carbon atoms and at least three hydroxy groups, and an unsaturated carboxylic acid. The crosslinking agent is set such that a molecular weight ratio of the main component to a standard compound is in the range of from 0.7/1 to less than 1.3/1. Here, the standard compound is defined as an ester composed of the polyhydroxy alcohol and the unsaturated carboxylic acid which compose the main component, in which all the hydroxy groups in the polyhydroxy alcohol are ester-linked with the unsaturated carboxylic acid.

It is not preferable to set the ratio of the molecular weight outside of the above mentioned range or to set the main component content in the crosslinking agent less than 90 percent by weight because the advantages of the process according to this invention cannot be ensured.

The above crosslinking agent either includes a high boiling-point compound including at least two polyhydroxy alcohol structures having at least three hydroxy groups in a range of from more than 0 percent to less than 10 percent by weight, or consists of only a compound including one polyhydroxy alcohol structure having at least three hydroxy groups. As the amount of high boiling-point compound increases, the viscosity of the crosslinking agent increases; however, a suitable viscosity of the crosslinking agent for the process of the present invention is in a range of from 10 cps to 60 cps at 25° C. If the high boiling-point compound is included more than the above range or the viscosity is above 60 cps, the advantages of the process according to the present invention cannot be achieved. The measuring method of the viscosity will be described later.

The commercially available unsaturated carboxylates having a plurality of functional groups (hereinafter referred to as multi-functional groups) are normally produced by the esterification of the polyhydroxy alcohols and unsaturated carboxylic acid, such as acrylate, or the transesterification of the polyhydroxy alcohol and unsaturated carboxylates. However, since these unsaturated carboxylates are of multi-functional groups, the resulting compound, i.e., a compound in which all the hydroxy groups are esterified cannot be produced at high yield. Therefore, commercially available compounds such as unsaturated carboxylates of multi-functional groups normally yield low purity and are mixtures of a plurality of components.

As examples, the inventors of the present invention examined a plurality kinds of trimethylolpropane triacrylates on the market with respect to the compositions thereof, and discovered that compounds of intermediates or by-products were included in each trimethylolpropane triacrylate in a ratio ranging from 20 percent to 25 percent, and the trimethylolpropane triacrylate was included only about 80 percent. Therefore, the advantages of the process according to the present invention cannot be achieved using the commercially available unsaturated carboxylates as the crosslinking agent in the second process for preparing an absorbent resin of the present invention.

The crosslinking agent used in the second process for preparing an absorbent resin of the present invention is prepared by increasing the content of the main component of the crosslinking agent by separating and purifying the commercially available unsaturated carboxylates of multi-functional groups in a simple manner, for example, by a column chromatography, using an adsorbent such as silica gel, zeolite, active carbon, etc., or by an extraction using an organic solvent.

Preferred examples of the alcohol having not more than six carbon atoms and at least three hydroxy groups used in preparing the crosslinking agent used in the second process for preparing an absorbent resin of the present invention include: glycerin, trimethylolethane, tetramethylolethane, trimethylolpropane, tetrahydroxyethane, pentaerythritol, etc. Among the above listed alcohols, trimethylolpropane is especially preferable. For the unsaturated carboxylic acid used in the preparation of the crosslinking agent, any of the previously listed hydrophilic unsaturated monomers having at least one carboxyl group may be used. However, acrylic acid is especially preferable.

Examples of the main component of the crosslinking agent used in the second process for preparing an absorbent resin of the present invention include unsaturated carboxylates of multi-functional groups composed of an alcohol having not more than six carbon atoms and at least three hydroxy groups as an alcohol component and an unsaturated carboxylic acid as an acid component. Examples of the main component also include: a mixture of glycerin tri(meth)acrylate and glycerin di(meth)acrylate, a mixture of trimethylolethane tri(meth)acrylate and trimethylolethane di(meth)acrylate, a mixture of tetramethylolethane tetra(meth)acrylate and tetramethylolethane tri(meth)acrylate, a mixture of trimethylolpropane tri(meth)acrylate and trimethylolpropane di(meth)acrylate, a mixture of tetrahydroxyethane tetra(meth)acrylate and tetrahydroxyethane tri(meth)acrylate and the like.

In the second process for preparing an absorbent resin of the present invention, when a crosslinking agent whose main component exhibits low affinity and solubility with the hydrophilic unsaturated monomer having at least one carboxyl group (especially in a neutralized form) is employed, the advantages of the process according to the present invention becomes particularly clear. It is preferable that the main component of the crosslinking agent has at least three polymerizable unsaturated bonds in order to obtain still improved properties such as its gel stability, water soluble component content, etc., of the resulting absorbent resin.

In the second process for preparing an absorbent resin composition, the crosslinking agent is used preferably in an amount ranging from 0.01 mole percent to mole percent with a more preferred range being from 0.05 mole percent to 1 mole percent of the hydrophilic unsaturated monomer having at least one carboxyl group.

In the described first and second processes for preparing an absorbent resin of the present invention, the crosslinking agent used in the polymerization process may be combined with a small amount of another crosslinking agent (hereinafter referred to as first auxiliary crosslinking agent) as long as the advantages of the process according to the present invention can be achieved. Examples of the first auxiliary crosslinking agent include: (poly)ethylene glycol diglycidyl ether, glycerol diglycidyl ether, ethylene glycol, polyethylene glycol, propylene glycol, glycerin, pentaerythritol, ethylene carbonate, propylenecarbonate, ethylenediamine, polyethyleneimine, glycidyl (meth)acrylate, and the like.

Additionally, a water soluble polymer such as starch, cellulose, derivatives thereof, polyacrylic acid, polyvinyl alcohol, etc., may be present in the aqueous solution of the hydrophilic unsaturated monomer in order to obtain a graft copolymer.

In polymerizing the hydrophilic unsaturated monomer having at least one carboxyl group in the presence of the crosslinking agent in the present invention, a bulk polymerization or precipitation polymerization may be employed. However, in consideration of the performance, the easiness of the control of polymerization, an aqueous polymerization for polymerizing the hydrophilic unsaturated monomer in an aqueous solution or a reverse-phase suspension polymerization are especially preferable, and the aqueous polymerization for polymerization in the aqueous solution without using an organic solvent is especially preferable. In this polymerization process, the hydrophilic unsaturated monomer is present in the aqueous solution in an amount ranging from 20 percent by weight to a saturation concentration, with a more preferred range being from 25 percent by weight to 40 percent by weight in order to make the advantages of the process according to the present invention greater.

In the polymerization process of the present invention, the following polymerization initiator may be used: a radical polymerization initiator such as potassium persulfate, ammonium persulfate, sodium persulfate, t-butyl hydroperoxide, hydrogen peroxide, 2,2'-azobis(2-aminodipropane) dihydrochloride, an active energy rays such as ultraviolet rays, electron rays, and the like. In the case of employing an oxidative radical polymerization initiator, a redox polymerization may be carried out by simultaneously using a reducing agent such as sodium sulfite, sodium bisulfite, ferrous sulfate, L-ascorbic acid, etc.

In order to enable the resulting absorbent resin to be treated as particles, the water content of the absorbent resin is set in a range of from 0.1 percent to 50 percent with a more preferred range being from 1 percent to 20 percent and the most preferred range being from 1 percent to 10 percent. Normally, the polymerization process is followed by a drying process.

In the process for preparing an absorbent resin of the present invention, the polymer resulting from the polymerization process is preferably heated at a temperature in the range of from 80° C. to 250° C. with a more preferred range being from 150° C. to 220° C. A heating temperature is set in the above range because if the polymer is heated at temperature above 250° C., the properties of the absorbent resin may be lowered and if the polymer is heated at a temperature below 80° C., a sufficient gel strength may not be achieved.

For the heating process, a generally used dryer or heater may be used such as a hot-air dryer, thin-type mix dryer, rotary dryer, disk dryer, fluidized-bed dryer, flash dryer, infra-red dryer, etc.

The resulting absorbent resin may have, for example, undefined, circular, fibrous, stick-like, or virtually circular shape. However, in consideration of the applications thereof to the sanitary goods with respect to the diffusivity of aqueous liquid, the resistance to moving out of the pulp, etc., it is preferable that the absorbent resin has an undefined shape with a preferred range of an average particle diameter being from 10 μm to 1000 μm and a more preferred range of an average particle diameter being from 300 μm to 600 μm.

In the present invention, in order to obtain a still improved absorbent properties of the resulting absorbent resin under pressure, such as a magnifier of absorbency, absorbing power, permeability to aqueous liquid, etc., the absorbent resin resulting from the process of the present invention may be mixed with a crosslinking agent which is reactive with a carboxyl group (hereinafter referred to as second auxiliary crosslinking agent) and heated as a vicinity of the surface of the absorbent resin is more strongly crosslinked. Examples of the second auxiliary crosslinking agent include the following known crosslinking agents: polyhydroxy alcohol compounds such as ethylene glycol, diethylene glycol, propylene glycol, triethylene glycol, tetraethylene glycol, polyethylene glycol, propylene glycol, 1,3-propanediol, dipropylene glycol, 2,2,4-trimethyl-1,3-pentadiol, polypropylene glycol, glycerin, polyglycerin, 2-butane-1,4-diol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene oxopropylene block copolymer, pentaerythritol, sorbitol, etc.; polyhydroxy epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, etc.; polyamine compounds such as ethylenediamine, diethylenetriamine, triethylenetetramine, tetraethylenepentamine, pentaethylenehexamine, polyethyleneimine, etc.; polyhydroxy isocyanate compounds such as 2,4-tolylene diisocyanate, hexamethylene diisocyanate, etc.; polyhydroxy oxazoline compounds such as 1,2-ethylenebisoxazoline, etc.; alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, 1,3-dioxopane-2-one, etc.; haloepoxy compounds such as epichlorohydrin, epibromehydrine, α-methylepichlorohydrin, etc.; metallic compounds such as hydroxides and chlorides of metals: zinc, calcium, magnesium, aluminum, iron, zirconium, etc.

In blending the second auxiliary crosslinking agent for crosslinking the vicinity of the surface, it is preferable that water is added either simultaneously or separately, and an insoluble particle powders, surface active agent, hydrophilic organic solvent, etc., may be used as well.

The first and second processes of the present invention for preparing the absorbent resin give improved properties of the absorbent resin: its gel stability, water soluble component content, etc. Although the factors which give the improvement of the above properties are not sure, the following is presumed to be the reason why the improved properties of the absorbent resin can be achieved: the affinity and solubility of the crosslinking agent to the hydrophilic unsaturated monomer having at least one carboxyl group can be improved significantly by the combined use of the second crosslinking agent and by adjusting the content of a high boiling-point compound, and thus a uniform crosslinking structure can be achieved.

Additionally, a deodorant, perfume, inorganic powder, foaming agent, pigment, dye, hydrophilic short fiber, synthetic fiber, fertilizer, oxidizing agent, reducing agent, water, salts, etc., may be added to the resulting absorbent resin prepared by the process of the present invention, which enables the absorbent resin to have various functions and thus applicable to other fields than the sanitary goods such as paper diaper, sanitary napkin, etc.

As described, the process in accordance with the present invention enables the absorbent resin to be prepared without having therein by-products such as the surface active agent, diffusants, etc., nor using a large amount of crosslinking agent.

Moreover, the resulting absorbent resin prepared by the described process according to the present invention exhibits excellent properties including its gel stability, water soluble component content, diffusivity of and permeability to aqueous liquid, suitable for use in sanitary goods. The absorbent resin prepared by the process of the present invention is suitable for use in sanitary goods such as paper diaper, sanitary napkin even when it is used in a larger amount.

EXAMPLES

The following examples and comparative examples are presented for the purpose of illustration only, and are not to be construed as limiting the scope of the invention in any way. The properties of the resulting absorbent resins were measured according to the procedures presented below.

Example 1

(a) absorbency

In a tea bag (40 mm×150 mm) made of a nonwoven material, 0.2 g of absorbent resin was uniformly fed, and the tea bag was put in 0.9 percent by weight of sodium chloride (physiologic saline) solution. After leaving the tea bag in the solution for 30 minutes, it was taken out and dewatered for a predetermined time. Then, the tea bag was weighted $W_1$. Another tea bag was prepared in the same manner without using the absorbent resin, and the above process was followed. Then, the tea bag was weighted $W_0$. Using the obtained two weights $W_0$ and $W_1$, the absorbency (g/g) of the absorbent resin was calculated through the following equation:

$$\text{absorbency (g/g)} = \frac{\text{weight } W_1 \text{ (g)} - \text{weight } W_0 \text{ (g)}}{\text{absorbent resin weight (g)}}$$

(b) gel strength

To 100 ml of synthetic urine, 1.0 g of absorbent resin was added, and after leaving it for an hour, the mixture was filtered off through a wire netting so as to obtain a swollen gel. Then, after extracting an excessive liquid from the swollen gel using paper, the swollen gel was set in a viscosity measuring unit (FLUID SPECTROMETER MODEL 8400 available from the Rheometric Co.) so as to measure a shearing modulus (kdyn/cm2), which represented the gel strength.

(c) gel stability

In a 100 ml of propylene container (diameter: 50 mm) with a cover, 2.0 g of absorbent resin was fed and urine collected from five adult persons was added so as to swell the absorbent resin. The container was closed with the cover and left for six hours at 40° C. Then, the container was inclined to a horizontal position and a distance (mm) the gel moved in one minute was measured, which represented the gel stability. Here, the shorter the distance the gel moves is, the more stable the swollen gel is in respect to the urine.

(d) water soluble component content

In 1000 ml of deionized water, 0.500 g of absorbent resin was diffused, and after agitating it for 16 hours, the mixture was filtered off through a filter paper, and the water soluble component content (percent) was calculated by a colloidal titration.

The crosslinking agent for the process of the present invention was prepared in the following manner.

Preparation 1

In an one-liter flask with four openings provided with an agitator, water-separator with a cooling tube, thermometer and air-introducing tube, 134 g of trimethylolpropane, 238 g of acrylic acid, 170 g of toluene, 24 g of p-toluenesulfonic acid and 0.6 g of hydroquinone were fed, and the flask was heated to 130° C. while introducing air thereinto.

Produced water was distilled off from a reaction system by an azeotropic dehydration with toluene, while observing the reaction by a gas chromatography (GC), and when the ratio by weight of the trimethylolpropane triacrylate to trimethylolpropane diacrylate reached 85/15, the reaction was stopped.

Then, the reaction solution was transferred to a separating funnel, and after neutralizing the unreacted acrylic acid with 500 g of 10 percent NaOH aqueous solution and 300 g of 5 percent NaOH aqueous solution, the reaction solution was layered and washed with water (500 g each) several times until the washed liquid was neutralized. Then, to an organic layer, 0.06 g of hydroquinone monomethyl ether was added, and the toluene was distilled under reduced pressure, thereby obtaining a reaction product.

The reaction product was analyzed using the GC, and a result of the calculation based on their peak area ratio gave the ratio of the trimethylolpropane triacrylate and trimethylolpropane diacrylate of 88/12 (by weight). The reaction product was also analyzed using a gel permeation chromatography (GPC). As a result a high boiling-point compound including at least two trimethylolpropane structures was contained 14 percent by weight.

Using the resulting crosslinking agent from Preparation 1, the hydrophilic unsaturated monomer having at least one carboxyl group was polymerized in the following manner:

In 414 g of acrylic acid (hydrophilic unsaturated monomer), 4.77 g of a crosslinking agent resulting from Preparation 1 was dissolved. To the mixture, 4382 g of 37 percent by weight of sodium acrylate and 699 g of ion exchange solution were added to give a reaction solution. In a stainless steel reactor of two-arms type kneader with a cover equipped with a jacket (volume content: 10 L) with two sigma blades, the reaction solution was poured, and the reaction system was displaced by introducing nitrogen gas while maintaining the reaction solution at 30° C. Then, while agitating the reaction solution maintained at 30° C., 2.40 g of sodium persulfate and 0.12 g of L-ascorbic acid were added to the reaction solution so as to start the polymerization. After leaving it for 60 minutes, a resulting finely divided water-containing gel-like polymer was taken out.

The resulting finely divided water-containing gel-like polymer was placed on a wire netting of 50 mesh and dried under hot air at 150° C. for 90 minutes. Then, the resulting dried polymer was pulverized by a vibrating mill and further classified by a wire netting of 20 mesh. As a result, an absorbent resin of undefined shape with a water content of 8 percent and an average particle diameter of 370 μm was obtained. The absorbency, gel strength, gel stability, water soluble component content (hereinafter simply referred to as results) of the resulting absorbent resin are presented in Table 1.

As is clear from the results, the absorbent resin resulting from Example 1 exhibits excellent properties: gel strength, gel stability, diffusivity of and permeability to aqueous liquid, and low water soluble component content.

Example 2

The same preparation procedure and analysis as in Example 1 were conducted except that the amount of use of the crosslinking agent in Example 1 was altered to 3.41 g, and an absorbent resin was obtained. The results of Example 2 are presented in Table 1.

Example 3

The same preparation procedure and analysis as in Example 1 were conducted except that the amount of use of the crosslinking agent in Example 1 was altered to 2.04 g, and an absorbent resin was obtained. The results of Example 3 are presented in Table 1.

Example 4

Preparation 2

The same preparation procedure as in Preparation 1 was conducted except that the reaction was stopped when the ratio of trimethylolpropane triacrylate to trimethylolpropane diacrylate reached 58/42 (by weight).

An obtained reaction product was analyzed using the GC, and the ratio of the methylolpropane triacrylate to trimethylolpropane diacrylate was calculated based on their peak area ratio, and the ratio of 62/38 (by weight) was obtained. The reaction product was also analyzed using a gel permeation chromatography (GPC). As a result, the reaction product includes 11 percent by weight of a high boiling-point compound including at least two trimethylolpropane structures.

The same preparation procedure and analysis as in Example 1 were conducted except that the crosslinking agent resulted from Preparation 2 was used in an amount of 3.41 g, and an absorbent resin was obtained. The results of Example 4 are presented in Table 1.

As is clear from the results of Examples 2 to 4, the absorbent resins resulting from Examples 2 to 4 exhibit excellent gel stability, low water soluble component content, and excellent diffusivity of and permeability to aqueous liquid as obtained from Example 1.

Comparative Example 1

Preparation 3

The same preparation procedure as in Preparation 1 was conducted except that the reaction was stopped when the ratio of trimethylolpropane triacrylate to trimethylolpropane diacrylate reached 97/3 (by weight).

The reaction product was analyzed using the GC, and the ratio of the methylolpropane triacrylate to trimethylolpropane diacrylate was calculated based on their peak area ratio, and the ratio of 98/2 (by weight) was obtained. The reaction product was also analyzed using a gel permeation chromatography (GPC). As a result a high boiling-point compound including at least two trimethylolpropane structures was contained 21 percent by weight.

Using 4.77 g of the crosslinking agent resulting from Preparation 3, the hydrophilic unsaturated monomer having at least one carboxyl group was polymerized as in the same manner as Example 1, and an absorbent resin was obtained. The results of Comparative Example 1 are presented in Table 1.

Comparative Example 2

The same preparation procedure and analysis as in Example 1 were conducted except that the crosslinking agent resulting from Preparation 3 was used in an amount of 3.41 g, and an absorbent resin was obtained. The results of Comparative Example 2 are presented in Table 1.

Comparative Example 3

The same preparation procedure and analysis as in Example 1 were conducted except that the crosslinking agent resulting from Preparation 3 was used in an amount of 2.04 g, and an absorbent resin was obtained. The results of Comparative Example 3 are presented in Table 1.

The results of Examples 1 to 4 and Comparative Examples 1 to 3 show that when the crosslinking agent is used outside the range of the ratio of the first crosslinking agent to the second crosslinking agent defined in the present invention as in the case of Comparative Examples 1 to 3, the resulting absorbent resins exhibit inferior properties including the gel stability, water soluble component content, and the diffusivity of and permeability to aqueous liquid compared with the absorbent resins resulting from Examples 1 to 4.

TABLE 1

| | Weight Ratio of First to Second Crosslinking Agents | Absorbency (g/g) | Gel Strength (kdyn/cm$^2$) | Gel Stability (mm) | Water Soluble Component Content (%) |
|---|---|---|---|---|---|
| Example No. | | | | | |
| 1 | 88/12 | 43 | 26 | 0 | 5 |
| 2 | 88/12 | 47 | 19 | 2 | 7 |
| 3 | 88/12 | 51 | 15 | 10 | 10 |
| 4 | 62/38 | 46 | 19 | 2 | 5 |
| Comparative Example No. | | | | | |
| 1 | 98/2 | 43 | 23 | 2 | 7 |
| 2 | 98/2 | 47 | 17 | 10 | 10 |
| 3 | 98/2 | 51 | 14 | 18 | 11 |

Example 5

The absorbency, gel stability and water soluble component content of a resulting absorbent resin were measured as in the same manner as Example 1 except that in testing the gel stability, the container was left for 24 hours instead of six hours.

The viscosity of the crosslinking agent was tested in the following manner: While maintaining the reaction vessel at 25° C. by circulating hot water in a thermostat, 1 ml of crosslinking agent was fed and set the reaction vessel in the viscosity measuring unit (VISCONIC EMD type available from Tokyo Keiki Ltd.). After leaving the reaction vessel for one minute, the viscosity was measured under predetermined conditions.

The crosslinking agent for the process of the present invention was prepared in the following manner.

Preparation 4

The same preparation procedure as in Preparation 1 was conducted except that the reaction was stopped when the total amount of trimethylolpropane triacrylate and trimethylolpropane diacrylate reached 83 percent by weight.

The reaction product was analyzed using the GC and GPC. As a result, the total content of trimethylolpropane triacrylate and trimethylolpropane diacrylate (which correspond to the crosslinking agent main component) was 83 percent by weight.

Then, using a glass column with a length of 500 mm which was filled with silica gel (No. 7734 available from Merk Co.), and an eluent of hexane/ethyl acetate=10/1 (vol/vol), the column chromatography was conducted so as to separate 20 g of the reaction product by each component. As a result, 15.0 g of trimethylolpropane triacrylate with a purity of 99 percent, molecular weight of 296 and molecular weight ratio of 1.0 which was a compound in which all the hydroxy groups in trimethylolpropane were ester-linked with acrylic acid was obtained.

Using chloroform/methane=25/1 (vol/vol) as an eluent, components adhering to the silica gel were eluted and the eluent was removed from the elute. As a result, 3.5 g of an organic substance was obtained. The organic substance was analyzed by the GPC and was presumed to be compounds with a molecular weight ranging from 400–1000. Furthermore, from this range of the molecular weight, the compounds were presumed to be polymerized compounds (with each molecular weight ratio in a range of from 1.35 to 3.88) which are the condensation products of trimethylolpropane triacrylate, trimethylolpropane diacrylate, trimethylolpropane monoacrylate, and the like. Namely, the organic substance is a high boiling-point compound.

Then, using the crosslinking agent resulting from Preparation 4, polymerization of the hydrophilic unsaturated monomer having at least one carboxyl group was conducted in manners presented below.

In 425 g of acrylic acid (hydrophilic unsaturated monomer), 4.88 g of trimethylolpropane triacrylate (99 percent purity) as a crosslinking agent resulting from Preparation 4 was dissolved. To the mixture, 4500 g of 37 percent by weight sodium acrylate and 540 g of ion exchange solution were added to give a reaction solution. In a reactor of a stainless steel kneader with a cover equipped with a jacket (volume content 10 L) with two sigma blades, the reaction solution was poured, and the reaction system was displaced by nitrogen gas while maintaining the reaction solution at 22° C. Then, the reaction solution kept at 22° C. was agitated, and 2.83 g of sodium persulfate and 0.12 g of L-ascorbic acid were added to the reaction solution so as to start the polymerization. After leaving the mixture for 40 minutes, the resulting finely divided water-containing gel-like polymer was taken out.

The finely divided water-containing gel-like polymer was placed on a wire netting of 50 mesh and dried under hot air at 150° C. for 90 minutes. Then, the resulting dried polymer was pulverized by a vibrating mill and further classified by a wire netting of 20 mesh. As a result, an absorbent resin of undefined shape was obtained. Reaction conditions such as amount and viscosity of the crosslinking agent, and respective contents of the crosslinking agent main component and the high boiling-point compound, and the properties of the resulting absorbent resin such as the absorbency, gel stability and water soluble component content (hereinafter simply referred to as results) are presented in Table 2.

As is clear from the results, the absorbent resin resulting from Example 5 exhibits excellent properties: gel stability, diffusivity of and permeability to aqueous liquid, and low water soluble component content.

Example 6

The same preparation procedure and analysis as in Example 5 were conducted except that a mixture of 4.68 g of trimethylolpropane triacrylate (99 percent purity) resulting from Preparation 4 and 0.20 g of the previously described organic substance was used as the crosslinking agent (main component content: 95 percent), and an absorbent resin was obtained. The results of Example 6 are presented in Table 2.

Example 7

The same preparation procedure and analysis as in Example 5 were conducted except that a mixture of 4.44 g of trimethylolpropane triacrylate (99 percent purity) resulting from Preparation 4 and 0.44 g of the organic substance was used as the crosslinking agent (main component content: 90 percent), and an absorbent resin was obtained. The results of Example 7 are presented in Table 2.

Example 8

The same preparation procedure and analysis as in Example 5 were conducted except that 6.98 g of trimethylolpropane triacrylate (99 percent purity) resulting from Preparation 4 was used as the crosslinking agent, and an absorbent resin was obtained. The results of Example 8 are presented in Table 2.

Example 9

The same preparation procedure and analysis as in Example 5 were conducted except that a mixture of 6.70 g of trimethylolpropane triacrylate (99 percent purity) resulting from Preparation 4 and 0.28 g of the organic substance was used as the crosslinking agent (with a main component content of 95 percent), and an absorbent resin was obtained. The results of Example 9 are presented in Table 2.

Example 10

The same preparation procedure and analysis as in Example 5 were conducted except that a mixture of 6.35 g of trimethylolpropane triacrylate (99 percent purity) resulting from Preparation 4 and 0.63 g of the organic substance was used as the crosslinking agent (main component content: 90 percent), and an absorbent resin was obtained. The results of Example 10 are presented in Table 2.

Example 11

The same preparation procedure and analysis as in Example 5 were conducted except that 3.49 g of trimethylolpropane triacrylate (99 percent purity) resulting from Preparation 4 was used as the crosslinking agent, and an absorbent resin was obtained. The results of Example 11 are presented in Table 2.

Example 12

The same preparation procedure and analysis as in Example 5 were conducted except that a mixture of 3.35 g of trimethylolpropane triacrylate (99 percent purity) resulting from Preparation 4 and 0.14 g of the organic substance was used as the crosslinking agent (main component content: 95 percent), and an absorbent resin was obtained. The results of Example 12 are presented in Table 2.

Example 13

The same preparation procedure and analysis as in Example 5 were conducted except that a mixture of 3.17 g of trimethylolpropane triacrylate (99 percent purity) resulting from Preparation 4 and 0.32 g of the organic substance was used as the crosslinking agent (main component content: 90 percent), and an absorbent resin was obtained. The results of Example 13 are presented in Table 2.

Example 14

Preparation 5

After obtaining a reaction product in the same manner as in Preparation 4, the reaction product was analyzed by the column chromatography using a solvent of hexane/ethyl acetate=3/2 (vol/vol) as in the same manner as in Preparation 4. As a result, 1.5 g of trimethylolpropane diacrylate with a molecular weight ratio of 0.82 (99 percent purity) was obtained from 30 g of the reaction product resulting from Preparation 4.

The same preparation procedure and analysis as in Example 5 were conducted except that a mixture of 4.15 g of trimethylolpropane triacrylate (99 percent purity) resulting from Preparation 4 and 0.73 g of trimethylolpropane diacrylate (99 percent purity) resulting from Preparation 5 was used as the crosslinking agent (main component content: 99 percent), and an absorbent resin was obtained. The results of Example 14 are presented in Table 2.

Example 15

The same preparation procedure and analysis as in Example 5 were conducted except that a mixture of 2.97 g of trimethylolpropane triacrylate (99 percent purity) resulting from Preparation 4 and 0.52 g of trimethylolpropane diacrylate (99 percent purity) resulting from Preparation 5 was used as the crosslinking agent (main component content: 99 percent), and the absorbent resin was obtained. The results of Example 15 are presented in Table 2.

Example 16

The same preparation procedure and analysis as in Example 5 were conducted except that a mixture of 5.93 g of trimethylolpropane triacrylate (99 percent purity) resulting from Preparation 4 and 1.05 g of trimethylolpropane triacrylate (99 percent purity) resulting from Preparation 5 was used as the crosslinking agent (main component content: 99 percent), and an absorbent resin was obtained. The results of Example 16 are presented in Table 2.

As is clear from the results of Examples 6 to 16, the absorbent resins resulting from Example 6 to 16 exhibit excellent properties: gel stability, diffusivity of and permeability to aqueous liquid, and low water soluble component content as in Example 5.

Comparative Example 4

The same preparation procedure and analysis as in Example 5 were conducted except that 4.88 g of trimethylolpropane triacrylate on the market (available from Rhone Poulenc, main component content: 80 percent) was used instead of the crosslinking agent of the present invention in Example 5, and an absorbent resin was obtained. The results of Comparative Example 4 are presented in Table 2.

Comparative Example 5

The same preparation procedure and analysis as in Example 5 were conducted except that a mixture of 2.69 g of trimethylolpropane triacrylate (99 percent purity) resulting from Preparation 4 and 0.80 g of the previously described organic substance was used as the crosslinking agent (main component content: 76 percent) instead of the crosslinking agent of the present invention used in Example 5, and an absorbent resin was obtained. The results of Comparative Example 5 are presented in Table 2.

Comparative Example 6

The same preparation procedure and analysis as in Example 5 were conducted except that a mixture of 4.23 g of trimethylolpropane triacrylate (99 percent purity) resulting from Preparation 4 and 2.75 g of the organic substance was used as the crosslinking agent (main component content: 60 percent) instead of the crosslinking agent of the present invention used in Example 5, and an absorbent resin was obtained. The results of Comparative Example 5 are presented in Table 2.

Comparative Example 7

The same preparation procedure and analysis as in Example 11 were conducted except that a mixture of 3.49 g of the reaction product resulting from Preparation 4, i.e., the reaction product with a total content of trimethylolpropane triacrylate and trimethylolpropane diacrylate of 85 percent by weight as the crosslinking agent instead of the crosslinking agent of the present invention used in Example 11, an the absorbent resin was obtained. The results of Comparative Example 5 are presented in Table 2.

The results of Examples 5 to 16 and Comparative Examples 4 to 7 show that when the commercially available crosslinking agent with low purity is used as in the Comparative Examples 4 to 7, the resulting absorbent resins exhibit inferior properties such as gel stability, water soluble component content, and diffusivity of and permeability to aqueous liquid as compared with the absorbent resins resulting from Examples 5 to 16.

TABLE 2

| | Crosslinking Agent Main Component Content (%) | High Boiling-point compound (%) | Crosslinking Agent Amount (mol %) | Absorbency (g/g) | Gel Stability (mm) | Water Soluble Component Content (%) | Viscosity of Crosslinking Agent |
|---|---|---|---|---|---|---|---|
| Example No. | | | | | | | |
| 5 | TMPTA 99 | 1 | 0.07 | 41 | 1 | 3 | 40 |
| 6 | 95 | 5 | 0.07 | 42 | 1 | 4 | 45 |
| 7 | 90 | 9 | 0.07 | 44 | 2 | 5 | 50 |
| 8 | 99 | 1 | 0.10 | 40 | 0 | 2 | 40 |
| 9 | 95 | 5 | 0.10 | 41 | 1 | 3 | 45 |
| 10 | 90 | 9 | 0.10 | 42 | 2 | 4 | 50 |
| 11 | 99 | 1 | 0.05 | 45 | 3 | 6 | 40 |
| 12 | 95 | 5 | 0.05 | 45 | 4 | 7 | 45 |
| 13 | 90 | 9 | 0.05 | 46 | 5 | 7 | 50 |
| 14 | TMPTA 84 TMPDA 15 Total 99 | 1 | 0.07 | 42 | 0 | 4 | 40 |
| 15 | TMPTA 84 TMPDA 15 Total 99 | 1 | 0.05 | 45 | 5 | 6 | 40 |
| 16 | TMPTA 84 TMPDA 15 Total 99 | 1 | 0.10 | 41 | 0 | 2 | 40 |
| Comparative Example No. | | | | | | | |
| 4 | TMPTA 80 | 20 | 0.07 | 42 | 7 | 6 | 103 |
| 5 | 76 | 24 | 0.05 | 45 | 12 | 8 | 96 |
| 6 | 60 | 40 | 0.10 | 44 | 10 | 7 | 110 |
| 7 | 85 | 15 | 0.05 | 46 | 11 | 10 | 87 |

TMPTA: trimethylolpropane triacrylate
TMPDA: trimethylolpropane diacrylate

The invention being thus described, it will be obvious that the same way be varied in many ways. Such variations are not to be regarded as a departure from the spirit and scope of the invention, and all such modifications as would be obvious to one skilled in the art are intended to be included within the scope of the following claims.

What is claimed is:

1. A process for preparing an absorbent resin comprising the steps of:

providing trimethylolpropane and acrylic acid;

producing a crosslinking agent by mixing and esterifying the trimethylolpropane and acrylic acid so that a ratio in weight percent of trimethylolpropane triacrylate and trimethylolpropane diacrylate is from 95/5 to 50/50; and polymerizing a hydrophilic unsaturated monomer having at least one carboxyl group in the presence of said crosslinking agent, thereby producing a crosslinked polymer.

2. The process according to claim 1, wherein the crosslinking agent includes a high boiling-point compound at a proportion in the range of from 10 weight percent to 20 weight percent, the high boiling-point compound including at least two trimethylolpropane radicals.

3. The process according to claim 1, wherein the hydrophilic unsaturated monomer is a material selected from the group consisting of acrylic acid, methacrylic acid, acrylic acid in a neutralized form and methacrylic acid in a neutralized form.

4. The process according to claim 1, wherein 30 mole percent to 90 mole percent of the carboxyl groups in the hydrophilic unsaturated monomer are neutralized.

5. The process according to claim 1, wherein 50 mole percent to 80 mole percent of the carboxyl groups in the hydrophilic unsaturated monomer are neutralized.

6. The process according to claim 1, wherein 60 mole percent to 75 mole percent of the carboxyl groups in the hydrophilic unsaturated monomer are neutralized.

7. The process according to claim 1, wherein the process for polymerizing the hydrophilic unsaturated monomer is carried out in an aqueous solution of the hydrophilic unsaturated monomer having a concentration ranging from 20 percent by weight to saturation.

8. The process according to claim 1, wherein the process for polymerizing the hydrophilic unsaturated monomer is carried out in an aqueous solution of the hydrophilic unsaturated monomer having a concentration ranging from 25 percent by weight to 40 percent by weight.

9. The process according to claim 1, further comprising the step of heating said crosslinked polymer at a temperature in the range of from 80° C. to 250° C.

10. The process according to claim 1, further comprising the step of heating said crosslinked polymer at a temperature in the range of from 150° C. to 220° C.

11. The process according to claim 1, wherein the amount of the crosslinking agent is 0.05 to 1 mole percent with respect to said hydrophilic unsaturated monomer.

12. The process of claim 1, wherein said hydrophilic unsaturated monomer is polymerized in the absence of surface active agents and dispersants.

13. A process for preparing an absorbent resin, comprising the steps of:

providing a hydrophilic unsaturated monomer having at least one carboxyl group;

providing a crosslinking agent which includes at least 90 percent by weight of a main component, the main component being an ester having at least two polymerizable unsaturated bonds, wherein:

the ester is based on:

a polyhydroxy alcohol having not more than six carbon atoms and at least three hydroxy groups; and an unsaturated carboxylic acid; and wherein the molecular weight of the main component is expressed as a molecular weight ratio of the main component to a standard compound, said ratio is in the range of from 0.7/1 to less than 1.3/1, wherein the standard compound is an ester based on:

the polyhydroxy alcohol that composes the main component, and the unsaturated carboxylic acid that composes the main component, in which all the hydroxy groups in the polyhydroxy alcohol are ester-linked with the unsaturated carboxylic acid, and polymerizing said hydrophilic unsaturated monomer in the presence of said crosslinking agent, thereby producing a crosslinked polymer.

14. The process according to claim 13, wherein said crosslinking agent further comprises a high boiling-point compound at a concentration of less than 10 percent by weight, the high boiling-point compound including at least two polyhydroxy alcohol radicals per molecular.

15. The process according to claim 13, wherein said crosslinking agent consists of only a compound including one polyhydroxy alcohol radical per molecule.

16. The process according to claim 13, wherein said crosslinking agent contains at least at 95 percent by weight of said main component.

17. The process according to claim 13, wherein said crosslinking agent has a viscosity of from 10 cps to 60 cps at 25° C.

18. The process according to claim 13, wherein said polyhydroxy alcohol is trimethylolpropane, and said unsaturated carboxylic acid is acrylic acid.

19. The process according to claim 13, wherein said crosslinking agent is used in an amount ranging from 0.01 mole percent to 5 mole percent with respect to said hydrophilic unsaturated monomer.

20. The process according to claim 13, wherein said crosslinking agent is used in an amount ranging from 0.05 mole percent to 1 mole percent with respect to said hydrophilic unsaturated monomer.

21. The process according to claim 13, wherein said hydrophilic unsaturated monomer is a material selected from the group consisting of acrylic acid, methacrylic acid, acrylic acid in a neutralized form and methacrylic acid in a neutralized form.

22. The process according to claim 13, wherein 30 mole percent to 90 mole percent of the carboxyl groups in the hydrophilic unsaturated monomer are neutralized.

23. The process according to claim 13, wherein 50 mole percent to 80 mole percent of the carboxyl groups in the hydrophilic unsaturated monomer are neutralized.

24. The process according to claim 13, wherein 60 mole percent to 75 mole percent of the carboxyl groups in the hydrophilic unsaturated monomer are neutralized.

25. The process according to claim 13, wherein the step of polymerizing the hydrophilic unsaturated monomer is carried out in an aqueous solution in which the hydrophilic unsaturated monomer has a concentration ranging from 20 percent by weight to saturation.

26. The process according to claim 13, wherein the step of polymerizing the hydrophilic unsaturated monomer is carried out in an aqueous solution in which the hydrophilic unsaturated monomer has a concentration ranging from 25 percent by weight to 40 percent by weight.

27. The process according to claim 13, further comprising heating said crosslinked polymer at a temperature in the range of from 80° C. to 250° C.

28. The process according to claim 13, further comprising heating said crosslinked polymer at a temperature in the range of from 150° C. to 220° C.

29. The process of claim 13, wherein said hydrophilic unsaturated monomer is polymerized in the absence of surface active agents and dispersants.

* * * * *